US008445641B2

(12) United States Patent
Drummy et al.

(10) Patent No.: US 8,445,641 B2
(45) Date of Patent: May 21, 2013

(54) NANOCOMPOSITES OF REPEAT SEQUENCE PROTEINS AND PHYLLOSILICATE CLAYS AND THEIR PREPARATION

(75) Inventors: Lawrence F. Drummy, Huber Heights, OH (US); Joseph C. McAuliffe, Sunnyvale, CA (US); Rajesh R. Naik, Centerville, OH (US); Richard A. Vaia, Beavercreek, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 935 days.

(21) Appl. No.: 11/990,665

(22) PCT Filed: Aug. 22, 2006

(86) PCT No.: PCT/US2006/032598
§ 371 (c)(1),
(2), (4) Date: Jul. 29, 2009

(87) PCT Pub. No.: WO2008/024105
PCT Pub. Date: Feb. 28, 2008

(65) Prior Publication Data
US 2009/0312455 A1 Dec. 17, 2009

Related U.S. Application Data

(60) Provisional application No. 60/710,308, filed on Aug. 22, 2005.

(51) Int. Cl.
*C07K 4/12* (2006.01)

(52) U.S. Cl.
USPC ........................................ 530/353

(58) Field of Classification Search
None
See application file for complete search history.

(56) References Cited

U.S. PATENT DOCUMENTS

| 5,243,038 A | 9/1993 | Ferrari et al. |
| 6,355,776 B1 | 3/2002 | Ferrari et al. |
| 6,521,690 B1 | 2/2003 | Ross et al. |
| 6,811,599 B2 | 11/2004 | Fischer et al. |
| 2004/0180027 A1* | 9/2004 | Kumar et al. .............. 424/70.14 |
| 2004/0223931 A1* | 11/2004 | Mondet et al. ................. 424/64 |

FOREIGN PATENT DOCUMENTS

| WO | WO2004/080426 | 9/2004 |
| WO | WO 2004/080426 A2 | 9/2004 |
| WO | WO 2004/080426 A3 | 9/2004 |
| WO | WO2004/104020 | 12/2004 |
| WO | WO2004/104021 | 12/2004 |
| WO | WO 2007/080426 A1 | 7/2007 |

OTHER PUBLICATIONS

Krikorian, Vahik et al., "Polypeptide-Based Nanocomposite: Structure and Properties of Poly(L-lysine)/Na+—Montmorillonite," J. Polym. Sci. Part B, vol. 40 No. 22 (2002) pp. 2579-2586.
Bertrand, Marylene et al., "Conformational Transition of Acidic Peptides Exposed to Minerals in Suspension," Chemistry, vol. 6 No. 18 (2000) pp. 3452-3455.
Andersson, L., et. al., "Large-scale synthesis of peptides", *Biopolymers*, 55(3): 227-50, 2000.
Bertrand, M., et al., "Conformation Transition of Acidic Peptides Exposed to Minerals in Suspension", *Chem. Eur. J.*, 6(18):3452-55, 2000.
Cappello, J., "Genetically Engineered Protein Polymers", in *Handbook of Biodegradable Polymers*, ed. by A.J. Domb et al., Amsterdam: Harwood Academic Pub., pp. 387-414, 1997.
Chen, P., et al., "Interaction and Properties of Highly Exfoliated Soy Protein/Montmorillonite Nanocomposites", *Biomacromolecules*, vol. 7(6): 1700-6, Jun. 2006.
Dohren, H.V., et al., "Multifunctional Peptide Synthase", *Chem. Rev.*, 97(7): 2675-2705, 1997.
Krikorian, V., et al. "Polypeptide-Based Nanocomposite: Structure and Properties of Poly(L-lysine)/Na+—Montmorillonite", *J. Polym. Sci. B: Polym. Phys.*, 40(22): 2579-2586, 2002.
Patil, A., et al., "Fabrication of functional protein-organoclay lamellar nanocomposites by biomolecule-induced assembly of exfoliated aminopropyl-functionalized magnesium phyllosilicates", *J. Mater. Chem.*, 15(35-36): 3838-3843, 2005.
Usuki, A., et al., "Synthesis of nylon 6-clay hybrid", *J. Mater. Res.*, 8(5): 1179-1184, May 1993.
Wong, C.H., et al., "New Developments in Enzymatic Peptide Synthesis", *Experientia*, 47(11-12): 1123-1129, 1991.

* cited by examiner

*Primary Examiner* — Christina Bradley
(74) *Attorney, Agent, or Firm* — AFMCLO/JAZ; Rebecca Greendyke

(57) ABSTRACT

Nanocomposites of repeat sequence protein polymers and phyllosilicates demonstrated improved material properties, for example, improved elasticity, and are useful as suture, tissue scaffolding, and biodegradable composite materials.

20 Claims, 5 Drawing Sheets

Figure 1. X-ray scattering curves for the MMT/SELP samples. The curves show a log-log slope of -2.1 in the small-angle regime. The wide-angle regime clearly shows some scattering from the amorphous SELP and the peak at 0.45 nm from the (110) and (200) planes of the MMT lattice. No inter-layer peak from the MMT sheets is seen, indicating exfoliation.

(a,b) Low and high magnification TEM images from a microtomed cross-section of a 2%MMT/SELP film. (c,d) Cross-section of a 4%MMT/SELP film. (e,f) Cross-section of an 8%MMT/SELP film. At high magnification individual, 1 nm thick, MMT layers can be seen edge on. At lower magnification, extremely uniform dispersion is seen in the films.

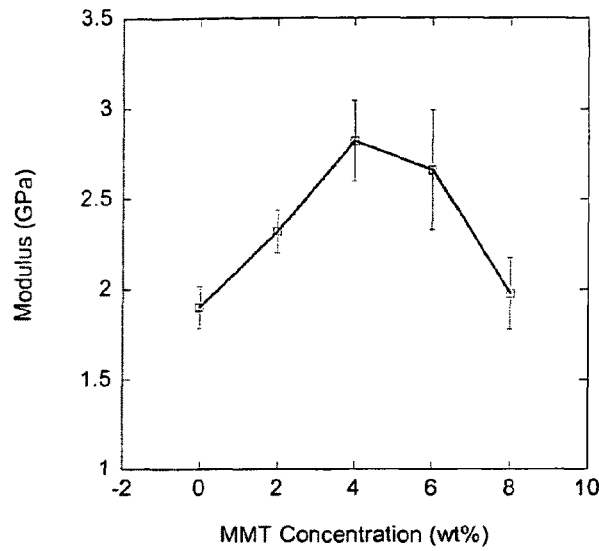

Figure 3a. Room temperature elastic modulus measured from tensile tests for the MMT/SELP samples. An improvement in stiffness from 2 GPa to nearly 3 GPa is seen at MMT concentrations of 4-6% by weight, however the modulus decreases with further addition of MMT.

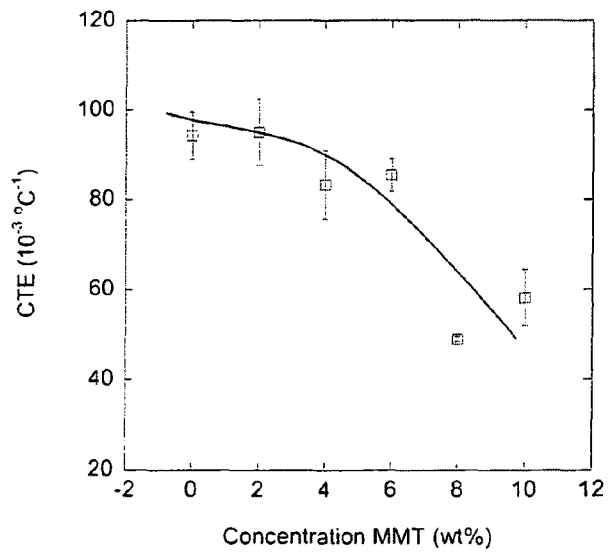

Figure 3b. Coefficient of thermal expansion (CTE) measured from thermal mechanical analysis in film/fiber geometry. The CTE in the rubbery region (>200C) shows a clear decrease with increasing MMT concentration.

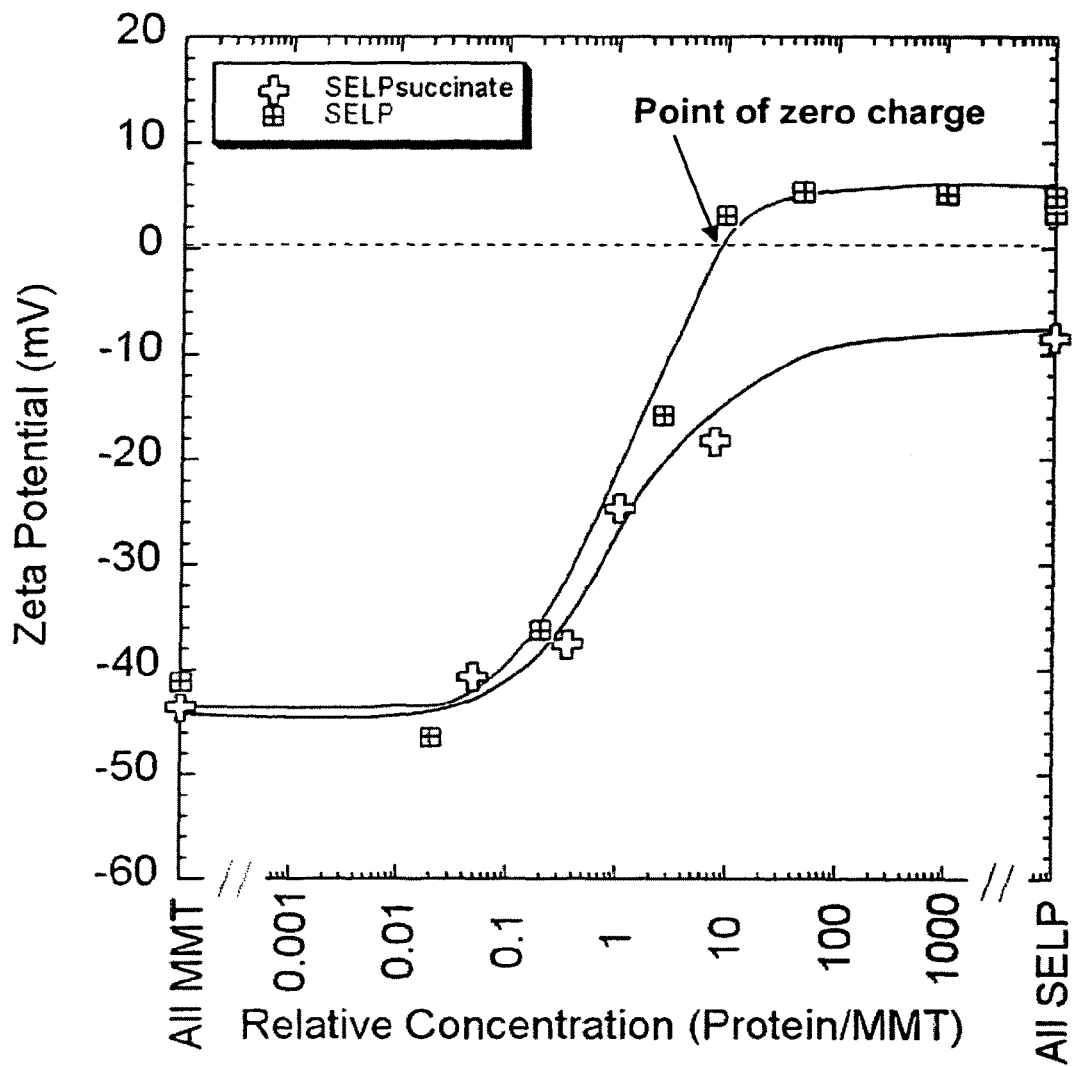
Figure 4. Plot of the zeta potential as a function of relative concentration (by weight) of SELP to MMT. As SELP is added to the MMT suspension, the negative surface charge of the MMT sheets is masked by the adsorbed SELP.

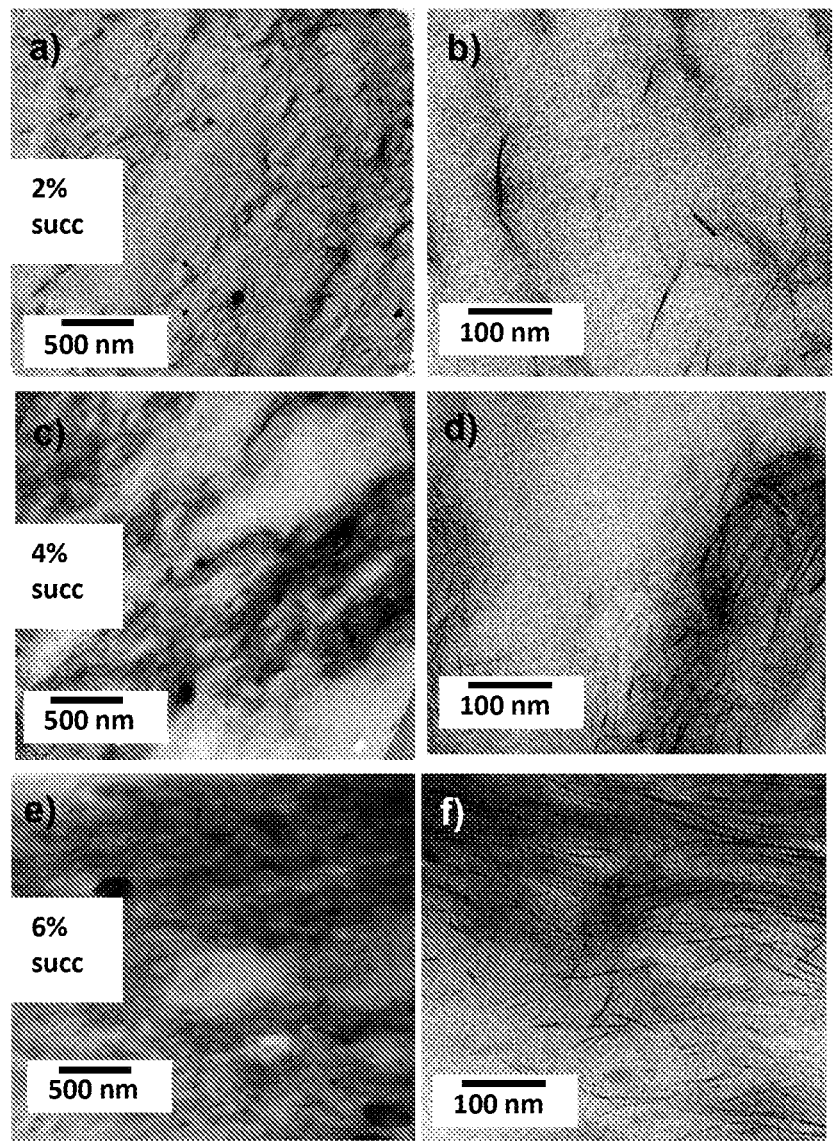
Figure 5. (a,b) Low and high magnification TEM images from a microtomed cross-section of a 2%MMT/SELPsucc film. (c,d) Cross-section of a 4%MMT/SELPsucc film. (e,f) Cross-section of a 6%MMT/SELPsucc film. At high magnification individual, 1 nm thick, MMT layers can be seen edge on. At lower magnification, some micron-scale phase separation is seen in the films.

```
                         SEQUENCE LISTING

<160> NUMBER OF SEQ ID NOS: 12

<210> SEQ ID NO 1
<211> LENGTH: 6
<212> TYPE: PRT
<213> ORGANISM: Artificial Sequence
<220> FEATURE:
<223> OTHER INFORMATION: Generated by expression of recombinant
      DNA in E. coli

<400> SEQUENCE: 1

Gly Ala Gly Ala Gly Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Generated by expression of recombinant
      DNA in E. coli

<400> SEQUENCE: 2

Gly Val Gly Val Pro
1               5

<210> SEQ ID NO 3
<211> LENGTH: 5
<212> TYPE: PRT
<213> ORGANISM: Artificial Sequence
<220> FEATURE:
<223> OTHER INFORMATION: Generated by expression of recombinant
      DNA in E. coli

<400> SEQUENCE: 3

Gly Lys Gly Val Pro
1               5

<210> SEQ ID NO 4
<211> LENGTH: 33
<212> TYPE: PRT
<213> ORGANISM: Artificial Sequence
<220> FEATURE:
<223> OTHER INFORMATION: Generated by expression of recombinant
      DNA in E. coli

<400> SEQUENCE: 4

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met

<210> SEQ ID NO 5
<211> LENGTH: 21
<212> TYPE: PRT
<213> ORGANISM: Artificial Sequence
<220> FEATURE:
<223> OTHER INFORMATION: Generated by expression of recombinant
      DNA in E. coli
```

-continued

```
<400> SEQUENCE: 5

Gly Ala Gly Ala Met Asp Pro Gly Arg Tyr Gln Asp Leu Arg Ser His
1               5                   10                  15

His His His His His
            20

<210> SEQ ID NO 6
<211> LENGTH: 886
<212> TYPE: PRT
<213> ORGANISM: Artificial Sequence
<220> FEATURE:
<221> NAME/KEY: REPEAT
<222> LOCATION: (34)..(865)
<223> OTHER INFORMATION: Generated by expression of recombinant
      DNA in E. coli

<400> SEQUENCE: 6

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ala Gly Ser Gly Ala Gly Ala Gly Ser Gly Val Gly
        35                  40                  45

Val Pro Gly Val Gly Val Pro Gly Val Gly Val Pro Gly Lys Gly Val
    50                  55                  60

Pro Gly Val Gly Val Pro Gly Val Gly Val Pro Gly Val Gly Val Pro
65                  70                  75                  80

Gly Val Gly Val Pro Gly Ala Gly Ala Gly Ser Gly Ala Gly Ala Gly
                85                  90                  95

Ser Gly Ala Gly Ala Gly Ser Gly Ala Gly Ala Gly Ser Gly Val Gly
            100                 105                 110

Val Pro Gly Val Gly Val Pro Gly Val Gly Val Pro Gly Lys Gly Val
        115                 120                 125

Pro Gly Val Gly Val Pro Gly Val Gly Val Pro Gly Val Gly Val Pro
    130                 135                 140

Gly Val Gly Val Pro Gly Ala Gly Ala Gly Ser Gly Ala Gly Ala Gly
145                 150                 155                 160

Ser Gly Ala Gly Ala Gly Ser Gly Ala Gly Ala Gly Ser Gly Val Gly
                165                 170                 175

Val Pro Gly Val Gly Val Pro Gly Val Gly Val Pro Gly Lys Gly Val
            180                 185                 190

Pro Gly Val Gly Val Pro Gly Val Gly Val Pro Gly Val Gly Val Pro
        195                 200                 205

Gly Val Gly Val Pro Gly Ala Gly Ala Gly Ser Gly Ala Gly Ala Gly
    210                 215                 220

Ser Gly Ala Gly Ala Gly Ser Gly Ala Gly Ala Gly Ser Gly Val Gly
225                 230                 235                 240

Val Pro Gly Val Gly Val Pro Gly Val Gly Val Pro Gly Lys Gly Val
                245                 250                 255

Pro Gly Val Gly Val Pro Gly Val Gly Val Pro Gly Val Gly Val Pro
            260                 265                 270

Gly Val Gly Val Pro Gly Ala Gly Ala Gly Ser Gly Ala Gly Ala Gly
        275                 280                 285

Ser Gly Ala Gly Ala Gly Ser Gly Ala Gly Ala Gly Ser Gly Val Gly
    290                 295                 300

Val Pro Gly Val Gly Val Pro Gly Val Gly Val Pro Gly Lys Gly Val
305                 310                 315                 320
```

```
Pro Gly Val Gly Val Pro Gly Val Gly Val Pro Gly Val Gly Val Pro
            325                 330                 335
Gly Val Gly Val Pro Gly Ala Gly Ala Gly Ser Gly Ala Gly Ala Gly
            340                 345                 350
Ser Gly Ala Gly Ala Gly Ser Gly Ala Gly Ala Gly Ser Gly Val Gly
            355                 360                 365
Val Pro Gly Val Gly Val Pro Gly Val Gly Val Pro Gly Lys Gly Val
        370                 375                 380
Pro Gly Val Gly Val Pro Gly Val Gly Val Pro Gly Val Gly Val Pro
385                 390                 395                 400
Gly Val Gly Val Pro Gly Ala Gly Ala Gly Ser Gly Ala Gly Ala Gly
                405                 410                 415
Ser Gly Ala Gly Ala Gly Ser Gly Ala Gly Ala Gly Ser Gly Val Gly
            420                 425                 430
Val Pro Gly Val Gly Val Pro Gly Val Gly Val Pro Gly Lys Gly Val
        435                 440                 445
Pro Gly Val Gly Val Pro Gly Val Gly Val Pro Gly Val Gly Val Pro
    450                 455                 460
Gly Val Gly Val Pro Gly Ala Gly Ala Gly Ser Gly Ala Gly Ala Gly
465                 470                 475                 480
Ser Gly Ala Gly Ala Gly Ser Gly Ala Gly Ala Gly Ser Gly Val Gly
            485                 490                 495
Val Pro Gly Val Gly Val Pro Gly Val Gly Val Pro Gly Lys Gly Val
        500                 505                 510
Pro Gly Val Gly Val Pro Gly Val Gly Val Pro Gly Val Gly Val Pro
            515                 520                 525
Gly Val Gly Val Pro Gly Ala Gly Ala Gly Ser Gly Ala Gly Ala Gly
        530                 535                 540
Ser Gly Ala Gly Ala Gly Ser Gly Ala Gly Ala Gly Ser Gly Val Gly
545                 550                 555                 560
Val Pro Gly Val Gly Val Pro Gly Val Gly Val Pro Gly Lys Gly Val
                565                 570                 575
Pro Gly Val Gly Val Pro Gly Val Gly Val Pro Gly Val Gly Val Pro
            580                 585                 590
Gly Val Gly Val Pro Gly Ala Gly Ala Gly Ser Gly Ala Gly Ala Gly
        595                 600                 605
Ser Gly Ala Gly Ala Gly Ser Gly Ala Gly Ala Gly Ser Gly Val Gly
    610                 615                 620
Val Pro Gly Val Gly Val Pro Gly Val Gly Val Pro Gly Lys Gly Val
625                 630                 635                 640
Pro Gly Val Gly Val Pro Gly Val Gly Val Pro Gly Val Gly Val Pro
                645                 650                 655
Gly Val Gly Val Pro Gly Ala Gly Ala Gly Ser Gly Ala Gly Ala Gly
            660                 665                 670
Ser Gly Ala Gly Ala Gly Ser Gly Ala Gly Ala Gly Ser Gly Val Gly
        675                 680                 685
Val Pro Gly Val Gly Val Pro Gly Val Gly Val Pro Gly Lys Gly Val
    690                 695                 700
Pro Gly Val Gly Val Pro Gly Val Gly Val Pro Gly Val Gly Val Pro
705                 710                 715                 720
Gly Val Gly Val Pro Gly Ala Gly Ala Gly Ser Gly Ala Gly Ala Gly
                725                 730                 735
Ser Gly Ala Gly Ala Gly Ser Gly Ala Gly Ala Gly Ser Gly Val Gly
```

```
                        740                 745                 750
Val Pro Gly Val Gly Val Pro Gly Val Pro Gly Lys Gly Val
            755                 760                 765

Pro Gly Val Gly Val Pro Gly Val Gly Val Pro Gly Val Gly Val Pro
            770                 775                 780

Gly Val Gly Val Pro Gly Ala Gly Ala Gly Ser Gly Ala Gly Ala Gly
785                 790                 795                 800

Ser Gly Ala Gly Ala Gly Ser Gly Ala Gly Ala Gly Ser Gly Val Gly
            805                 810                 815

Val Pro Gly Val Gly Val Pro Gly Val Gly Val Pro Gly Lys Gly Val
            820                 825                 830

Pro Gly Val Gly Val Pro Gly Val Gly Val Pro Gly Val Gly Val Pro
            835                 840                 845

Gly Val Gly Val Pro Gly Ala Gly Ala Gly Ser Gly Ala Gly Ala Gly
            850                 855                 860

Ser Gly Ala Gly Ala Met Asp Pro Gly Arg Tyr Gln Asp Leu Arg Ser
865                 870                 875                 880

His His His His His His
            885

<210> SEQ ID NO 7
<211> LENGTH: 884
<212> TYPE: PRT
<213> ORGANISM: Artificial Sequence
<220> FEATURE:
<221> NAME/KEY: REPEAT
<222> LOCATION: (34)..(864)
<223> OTHER INFORMATION: Generated by expression of recombinant
      DNA in E. coli and site-directed mutagenesis

<400> SEQUENCE: 7

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Val Gly Val Pro
            35                  40                  45

Gly Val Gly Val Pro Gly Val Gly Val Pro Gly Val Gly Val Pro Gly
50                  55                  60

Glu Gly Val Pro Gly Val Gly Val Pro Gly Val Gly Glu Pro Gly Val
65                  70                  75                  80

Gly Val Pro Gly Ala Gly Ala Gly Ser Gly Ala Gly Ala Gly Ser Gly
            85                  90                  95

Ala Gly Ala Gly Ser Gly Ala Gly Ala Gly Ser Gly Val Gly Val Pro
            100                 105                 110

Gly Val Gly Val Pro Gly Val Gly Val Pro Gly Val Gly Val Pro Gly
            115                 120                 125

Glu Gly Val Pro Gly Val Gly Val Pro Gly Val Gly Glu Pro Gly Val
            130                 135                 140

Gly Val Pro Gly Ala Gly Ala Gly Ser Gly Ala Gly Ala Gly Ser Gly
145                 150                 155                 160

Ala Gly Ala Gly Ser Gly Ala Gly Ala Gly Ser Gly Val Gly Val Pro
            165                 170                 175

Gly Val Gly Val Pro Gly Val Gly Val Pro Gly Val Gly Val Pro Gly
            180                 185                 190

Glu Gly Val Pro Gly Val Gly Val Pro Gly Val Gly Glu Pro Gly Val
            195                 200                 205
```

-continued

```
Gly Val Pro Gly Ala Gly Ala Gly Ser Gly Ala Gly Ala Gly Ser Gly
        210                 215                 220

Ala Gly Ala Gly Ser Gly Ala Gly Ala Gly Ser Gly Val Gly Val Pro
225                 230                 235                 240

Gly Val Gly Val Pro Gly Val Gly Val Pro Gly Val Gly Val Pro Gly
                245                 250                 255

Glu Gly Val Pro Gly Val Gly Val Pro Gly Val Gly Glu Pro Gly Val
                260                 265                 270

Gly Val Pro Gly Ala Gly Ala Gly Ser Gly Ala Gly Ala Gly Ser Gly
            275                 280                 285

Ala Gly Ala Gly Ser Gly Ala Gly Ala Gly Ser Gly Val Gly Val Pro
        290                 295                 300

Gly Val Gly Val Pro Gly Val Gly Val Pro Gly Val Gly Val Pro Gly
305                 310                 315                 320

Glu Gly Val Pro Gly Val Gly Val Pro Gly Val Gly Glu Pro Gly Val
                325                 330                 335

Gly Val Pro Gly Ala Gly Ala Gly Ser Gly Ala Gly Ala Gly Ser Gly
            340                 345                 350

Ala Gly Ala Gly Ser Gly Ala Gly Ala Gly Ser Gly Val Gly Val Pro
        355                 360                 365

Gly Val Gly Val Pro Gly Val Gly Val Pro Gly Val Gly Val Pro Gly
    370                 375                 380

Glu Gly Val Pro Gly Val Gly Val Pro Gly Val Gly Glu Pro Gly Val
385                 390                 395                 400

Gly Val Pro Gly Ala Gly Ala Gly Ser Gly Ala Gly Ala Gly Ser Gly
                405                 410                 415

Ala Gly Ala Gly Ser Gly Ala Gly Ala Gly Ser Gly Val Gly Val Pro
            420                 425                 430

Gly Val Gly Val Pro Gly Val Gly Val Pro Gly Val Gly Val Pro Gly
        435                 440                 445

Glu Gly Val Pro Gly Val Gly Val Pro Gly Val Gly Glu Pro Gly Val
    450                 455                 460

Gly Val Pro Gly Ala Gly Ala Gly Ser Gly Ala Gly Ala Gly Ser Gly
465                 470                 475                 480

Ala Gly Ala Gly Ser Gly Ala Gly Ala Gly Ser Gly Val Gly Val Pro
                485                 490                 495

Gly Val Gly Val Pro Gly Val Gly Val Pro Gly Val Gly Val Pro Gly
            500                 505                 510

Glu Gly Val Pro Gly Val Gly Val Pro Gly Val Gly Glu Pro Gly Val
        515                 520                 525

Gly Val Pro Gly Ala Gly Ala Gly Ser Gly Ala Gly Ala Gly Ser Gly
    530                 535                 540

Ala Gly Ala Gly Ser Gly Ala Gly Ala Gly Ser Gly Val Gly Val Pro
545                 550                 555                 560

Gly Val Gly Val Pro Gly Val Gly Val Pro Gly Val Gly Val Pro Gly
                565                 570                 575

Glu Gly Val Pro Gly Val Gly Val Pro Gly Val Gly Glu Pro Gly Val
            580                 585                 590

Gly Val Pro Gly Ala Gly Ala Gly Ser Gly Ala Gly Ala Gly Ser Gly
        595                 600                 605

Ala Gly Ala Gly Ser Gly Ala Gly Ala Gly Ser Gly Val Gly Val Pro
    610                 615                 620

Gly Val Gly Val Pro Gly Val Gly Val Pro Gly Val Gly Val Pro Gly
```

```
                625                 630                 635                 640
Glu Gly Val Pro Gly Val Gly Val Pro Gly Val Gly Glu Pro Gly Val
                    645                 650                 655
Gly Val Pro Gly Ala Gly Ala Gly Ser Gly Ala Gly Ala Gly Ser Gly
                660                 665                 670
Ala Gly Ala Gly Ser Gly Ala Gly Ala Gly Ser Gly Val Gly Val Pro
            675                 680                 685
Gly Val Gly Val Pro Gly Val Gly Val Pro Gly Val Gly Val Pro Gly
        690                 695                 700
Glu Gly Val Pro Gly Val Gly Val Pro Gly Val Gly Glu Pro Gly Val
705                 710                 715                 720
Gly Val Pro Gly Ala Gly Ala Gly Ser Gly Ala Gly Ala Gly Ser Gly
                725                 730                 735
Ala Gly Ala Gly Ser Gly Ala Gly Ala Gly Ser Gly Val Gly Val Pro
            740                 745                 750
Gly Val Gly Val Pro Gly Val Gly Val Pro Gly Val Gly Val Pro Gly
        755                 760                 765
Glu Gly Val Pro Gly Val Gly Val Pro Gly Val Gly Glu Pro Gly Val
    770                 775                 780
Gly Val Pro Gly Ala Gly Ala Gly Ser Gly Ala Gly Ala Gly Ser Gly
785                 790                 795                 800
Ala Gly Ala Gly Ser Gly Ala Gly Ala Gly Ser Gly Val Gly Val Pro
                805                 810                 815
Gly Val Gly Val Pro Gly Val Gly Val Pro Gly Val Gly Val Pro Gly
            820                 825                 830
Glu Gly Val Pro Gly Val Gly Val Pro Gly Val Gly Glu Pro Gly Val
        835                 840                 845
Gly Val Pro Gly Ala Gly Ala Gly Ser Gly Ala Gly Ala Gly Ser Gly
    850                 855                 860
Ala Gly Ala Met Asp Pro Gly Arg Tyr Gln Asp Leu Arg Ser His His
865                 870                 875                 880
His His His His

<210> SEQ ID NO 8
<211> LENGTH: 244
<212> TYPE: PRT
<213> ORGANISM: Artificial Sequence
<220> FEATURE:
<221> NAME/KEY: REPEAT
<222> LOCATION: (34)..(223)
<223> OTHER INFORMATION: Generated by expression of recombinant
      DNA in E. coli

<400> SEQUENCE: 8

Met Asp Pro Val Val Leu Gln Arg Arg Asp Trp Glu Asn Pro Gly Val
1               5                   10                  15
Thr Gln Leu Asn Arg Leu Ala Ala His Pro Pro Phe Ala Ser Asp Pro
                20                  25                  30
Met Gly Ala Gly Ser Gly Ala Gly Ala Gly Ser Gly Val Gly Val Pro
            35                  40                  45
Gly Val Gly Val Pro Gly Val Gly Val Pro Gly Val Gly Val Pro Gly
        50                  55                  60
Lys Gly Val Pro Gly Val Gly Val Pro Gly Val Gly Val Pro Gly Val
65                  70                  75                  80
Gly Val Pro Gly Ala Gly Ala Gly Ser Gly Ala Gly Ala Gly Ser Gly
                85                  90                  95
```

-continued

```
Ala Gly Ala Gly Ser Gly Ala Gly Ala Gly Ser Gly Val Gly Val Pro
            100                 105                 110
Gly Val Gly Val Pro Gly Val Gly Val Pro Gly Val Gly Val Pro Gly
        115                 120                 125
Lys Gly Val Pro Gly Val Gly Val Pro Gly Val Gly Val Pro Gly Val
    130                 135                 140
Gly Val Pro Gly Ala Gly Ala Gly Ser Gly Ala Gly Ala Gly Ser Gly
145                 150                 155                 160
Ala Gly Ala Gly Ser Gly Ala Gly Ala Gly Ser Gly Val Gly Val Pro
                165                 170                 175
Gly Val Gly Val Pro Gly Val Gly Val Pro Gly Val Gly Val Pro Gly
            180                 185                 190
Lys Gly Val Pro Gly Val Gly Val Pro Gly Val Gly Val Pro Gly Val
        195                 200                 205
Gly Val Pro Gly Ala Gly Ala Gly Ser Gly Ala Gly Ala Gly Ser Gly
    210                 215                 220
Ala Gly Ala Met Asp Pro Gly Arg Tyr Gln Asp Leu Arg Ser His His
225                 230                 235                 240
His His His His

<210> SEQ ID NO 9
<211> LENGTH: 246
<212> TYPE: PRT
<213> ORGANISM: Artificial Sequence
<220> FEATURE:
<221> NAME/KEY: REPEAT
<222> LOCATION: (34)..(225)
<223> OTHER INFORMATION: Generated by expression of recombinant
      DNA in E. coli and site-directed mutagenesis

<400> SEQUENCE: 9

Met Asp Pro Val Val Leu Gln Arg Arg Asp Trp Glu Asn Pro Gly Val
1               5                   10                  15
Thr Gln Leu Asn Arg Leu Ala Ala His Pro Pro Phe Ala Ser Asp Pro
            20                  25                  30
Met Gly Ala Gly Ala Gly Ser Gly Ala Gly Ala Gly Ser Gly Val Gly
        35                  40                  45
Val Pro Gly Val Gly Val Pro Gly Val Gly Val Pro Gly Val Gly Val
    50                  55                  60
Pro Gly Arg Gly Val Pro Gly Val Gly Val Pro Gly Val Gly Val Pro
65                  70                  75                  80
Gly Val Gly Val Pro Gly Ala Gly Ala Gly Ser Gly Ala Gly Ala Gly
                85                  90                  95
Ser Gly Ala Gly Ala Gly Ser Gly Ala Gly Ala Gly Ser Gly Val Gly
            100                 105                 110
Val Pro Gly Val Gly Val Pro Gly Val Gly Val Pro Gly Val Gly Val
        115                 120                 125
Pro Gly Arg Gly Val Pro Gly Val Gly Val Pro Gly Val Gly Val Pro
    130                 135                 140
Gly Val Gly Val Pro Gly Ala Gly Ala Gly Ser Gly Ala Gly Ala Gly
145                 150                 155                 160
Ser Gly Ala Gly Ala Gly Ser Gly Ala Gly Ala Gly Ser Gly Val Gly
                165                 170                 175
Val Pro Gly Val Gly Val Pro Gly Val Gly Val Pro Gly Val Gly Val
            180                 185                 190
Pro Gly Arg Gly Val Pro Gly Val Gly Val Pro Gly Val Gly Val Pro
        195                 200                 205
```

```
Gly Val Gly Val Pro Gly Ala Gly Ala Gly Ser Gly Ala Gly Ala Gly
    210                 215                 220

Ser Gly Ala Gly Ala Met Asp Pro Gly Arg Tyr Gln Asp Leu Arg Ser
225                 230                 235                 240

His His His His His His
        245

<210> SEQ ID NO 10
<211> LENGTH: 246
<212> TYPE: PRT
<213> ORGANISM: Artificial Sequence
<220> FEATURE:
<221> NAME/KEY: REPEAT
<222> LOCATION: (34)..(225)
<223> OTHER INFORMATION: Generated by expression of recombinant
      DNA in E. coli and site-directed mutagenesis

<400> SEQUENCE: 10

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ala Gly Ser Gly Ala Gly Ala Gly Ser Gly Val Gly
        35                  40                  45

Val Pro Gly Val Gly Val Pro Gly Val Gly Val Pro Gly Val Gly Val
    50                  55                  60

Pro Gly Glu Gly Val Pro Gly Val Gly Val Pro Gly Val Gly Val Pro
65                  70                  75                  80

Gly Val Gly Val Pro Gly Ala Gly Ala Gly Ser Gly Ala Gly Ala Gly
                85                  90                  95

Ser Gly Ala Gly Ala Gly Ser Gly Ala Gly Ala Gly Ser Gly Val Gly
            100                 105                 110

Val Pro Gly Val Gly Val Pro Gly Val Gly Val Pro Gly Val Gly Val
        115                 120                 125

Pro Gly Glu Gly Val Pro Gly Val Gly Val Pro Gly Val Gly Val Pro
    130                 135                 140

Gly Val Gly Val Pro Gly Ala Gly Ala Gly Ser Gly Ala Gly Ala Gly
145                 150                 155                 160

Ser Gly Ala Gly Ala Gly Ser Gly Ala Gly Ala Gly Ser Gly Val Gly
                165                 170                 175

Val Pro Gly Val Gly Val Pro Gly Val Gly Val Pro Gly Val Gly Val
            180                 185                 190

Pro Gly Glu Gly Val Pro Gly Val Gly Val Pro Gly Val Gly Val Pro
        195                 200                 205

Gly Val Gly Val Pro Gly Ala Gly Ala Gly Ser Gly Ala Gly Ala Gly
    210                 215                 220

Ser Gly Ala Gly Ala Met Asp Pro Gly Arg Tyr Gln Asp Leu Arg Ser
225                 230                 235                 240

His His His His His His
        245

<210> SEQ ID NO 11
<211> LENGTH: 965
<212> TYPE: PRT
<213> ORGANISM: Artificial Sequence
<220> FEATURE:
<221> NAME/KEY: REPEAT
<222> LOCATION: (34)..(943)
<223> OTHER INFORMATION: Generated by expression of recombinant
```

DNA in E. coli and site-directed mutagenesis

<400> SEQUENCE: 11

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Val Gly Val Pro Gly Val Gly Val Pro Gly Val Gly Val Pro
        35                  40                  45

Gly Val Gly Val Pro Gly Val Gly Val Pro Gly Val Gly Val Pro Gly
    50                  55                  60

Val Gly Val Pro Gly Val Gly Val Pro Gly Ala Gly Ala Gly Ser Gly
65                  70                  75                  80

Ala Gly Ala Gly Ser Gly Ala Gly Ala Gly Ser Gly Ala Gly Ala Gly
                85                  90                  95

Ser Gly Ala Gly Ala Gly Ser Gly Val Gly Val Pro Gly Val Gly Val
            100                 105                 110

Pro Gly Val Gly Val Pro Gly Val Gly Val Pro Gly Val Gly Val Pro
        115                 120                 125

Gly Val Gly Val Pro Gly Val Gly Val Pro Gly Val Gly Val Pro Gly
    130                 135                 140

Ala Gly Ala Gly Ser Gly Ala Gly Ala Gly Ser Gly Ala Gly Ala Gly
145                 150                 155                 160

Ser Gly Ala Gly Ala Gly Ser Gly Ala Gly Ala Gly Ser Gly Val Gly
                165                 170                 175

Val Pro Gly Val Gly Val Pro Gly Val Gly Val Pro Gly Val Gly Val
            180                 185                 190

Pro Gly Val Gly Val Pro Gly Val Gly Val Pro Gly Val Gly Val Pro
        195                 200                 205

Gly Val Gly Val Pro Gly Ala Gly Ala Gly Ser Gly Ala Gly Ala Gly
    210                 215                 220

Ser Gly Ala Gly Ala Gly Ser Gly Ala Gly Ala Gly Ser Gly Ala Gly
225                 230                 235                 240

Ala Gly Ser Gly Val Gly Val Pro Gly Val Gly Val Pro Gly Val Gly
                245                 250                 255

Val Pro Gly Val Gly Val Pro Gly Val Gly Val Pro Gly Val Gly Val
            260                 265                 270

Pro Gly Val Gly Val Pro Gly Val Gly Val Pro Gly Ala Gly Ala Gly
        275                 280                 285

Ser Gly Ala Gly Ala Gly Ser Gly Ala Gly Ala Gly Ser Gly Ala Gly
    290                 295                 300

Ala Gly Ser Gly Ala Gly Ala Gly Ser Gly Val Gly Val Pro Gly Val
305                 310                 315                 320

Gly Val Pro Gly Val Gly Val Pro Gly Val Gly Val Pro Gly Val Gly
                325                 330                 335

Val Pro Gly Val Gly Val Pro Gly Val Gly Val Pro Gly Val Gly Val
            340                 345                 350

Pro Gly Ala Gly Ala Gly Ser Gly Ala Gly Ala Gly Ser Gly Ala Gly
        355                 360                 365

Ala Gly Ser Gly Ala Gly Ala Gly Ser Gly Ala Gly Ala Gly Ser Gly
    370                 375                 380

Val Gly Val Pro Gly Val Gly Val Pro Gly Val Gly Val Pro Gly Val
385                 390                 395                 400

Gly Val Pro Gly Val Gly Val Pro Gly Val Gly Val Pro Gly Val Gly
```

```
                  405                 410                 415
Val Pro Gly Val Gly Val Pro Gly Ala Gly Ala Gly Ser Gly Ala Gly
                420                 425                 430

Ala Gly Ser Gly Ala Gly Ala Gly Ser Gly Ala Gly Ala Gly Ser Gly
            435                 440                 445

Ala Gly Ala Gly Ser Gly Val Gly Val Pro Gly Val Gly Val Pro Gly
        450                 455                 460

Val Gly Val Pro Gly Val Gly Val Pro Gly Val Gly Val Pro Gly Val
465                 470                 475                 480

Gly Val Pro Gly Val Gly Val Pro Gly Val Gly Val Pro Gly Ala Gly
                485                 490                 495

Ala Gly Ser Gly Ala Gly Ala Gly Ser Gly Ala Gly Ala Gly Ser Gly
            500                 505                 510

Ala Gly Ala Gly Ser Gly Ala Gly Ala Gly Ser Gly Val Gly Val Pro
        515                 520                 525

Gly Val Gly Val Pro Gly Val Gly Val Pro Gly Val Gly Val Pro Gly
    530                 535                 540

Val Gly Val Pro Gly Val Gly Val Pro Gly Val Gly Val Pro Gly Val
545                 550                 555                 560

Gly Val Pro Gly Ala Gly Ala Gly Ser Gly Ala Gly Ala Gly Ser Gly
                565                 570                 575

Ala Gly Ala Gly Ser Gly Ala Gly Ala Gly Ser Gly Ala Gly Ala Gly
            580                 585                 590

Ser Gly Val Gly Val Pro Gly Val Gly Val Pro Gly Val Gly Val Pro
        595                 600                 605

Gly Val Gly Val Pro Gly Val Gly Val Pro Gly Val Gly Val Pro Gly
    610                 615                 620

Val Gly Val Pro Gly Val Gly Val Pro Gly Ala Gly Ala Gly Ser Gly
625                 630                 635                 640

Ala Gly Ala Gly Ser Gly Ala Gly Ala Gly Ser Gly Ala Gly Ala Gly
                645                 650                 655

Ser Gly Ala Gly Ala Gly Ser Gly Val Gly Val Pro Gly Val Gly Val
            660                 665                 670

Pro Gly Val Gly Val Pro Gly Val Gly Val Pro Gly Val Gly Val Pro
        675                 680                 685

Gly Val Gly Val Pro Gly Val Gly Val Pro Gly Val Gly Val Pro Gly
    690                 695                 700

Ala Gly Ala Gly Ser Gly Ala Gly Ala Gly Ser Gly Ala Gly Ala Gly
705                 710                 715                 720

Ser Gly Ala Gly Ala Gly Ser Gly Ala Gly Ala Gly Ser Gly Val Gly
                725                 730                 735

Val Pro Gly Val Gly Val Pro Gly Val Gly Val Pro Gly Val Gly Val
            740                 745                 750

Pro Gly Val Gly Val Pro Gly Val Gly Val Pro Gly Val Gly Val Pro
        755                 760                 765

Gly Val Gly Val Pro Gly Ala Gly Ala Gly Ser Gly Ala Gly Ala Gly
    770                 775                 780

Ser Gly Ala Gly Ala Gly Ser Gly Ala Gly Ala Gly Ser Gly Ala Gly
785                 790                 795                 800

Ala Gly Ser Gly Val Gly Val Pro Gly Val Gly Val Pro Gly Val Gly
                805                 810                 815

Val Pro Gly Val Gly Val Pro Gly Val Gly Val Pro Gly Val Gly Val
            820                 825                 830
```

-continued

```
Pro Gly Val Gly Val Pro Gly Val Gly Val Pro Gly Ala Gly Ala Gly
        835                 840                 845

Ser Gly Ala Gly Ala Gly Ser Gly Ala Gly Ala Gly Ser Gly Ala Gly
    850                 855                 860

Ala Gly Ser Gly Ala Gly Ala Gly Ser Gly Val Gly Val Pro Gly Val
865                 870                 875                 880

Gly Val Pro Gly Val Gly Val Pro Gly Val Gly Val Pro Gly Val Gly
                885                 890                 895

Val Pro Gly Val Gly Val Pro Gly Val Gly Val Pro Gly Val Gly Val
            900                 905                 910

Pro Gly Ala Gly Ala Gly Ser Gly Ala Gly Ala Gly Ser Gly Ala Gly
        915                 920                 925

Ala Gly Ser Gly Ala Gly Ala Gly Ser Gly Ala Gly Ala Gly Ser Met
    930                 935                 940

Asp Pro Gly Arg Tyr Gln Leu Ser Ala Gly Arg Tyr His Tyr Gln Leu
945                 950                 955                 960

Val Trp Cys Gln Lys
        965

<210> SEQ ID NO 12
<211> LENGTH: 1038
<212> TYPE: PRT
<213> ORGANISM: Artificial Sequence
<220> FEATURE:
<221> NAME/KEY: REPEAT
<222> LOCATION: (34)..(1021)
<223> OTHER INFORMATION: Generated by expression of recombinant
      DNA in E. coli

<400> SEQUENCE: 12

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Val Gly Val Pro Gly Val Gly Val Pro Gly Val Gly Val Pro
        35                  40                  45

Gly Val Gly Val Pro Gly Lys Gly Val Pro Gly Val Gly Val Pro Gly
    50                  55                  60

Val Gly Val Pro Gly Val Gly Val Pro Gly Ala Gly Ala Gly Ser Gly
65                  70                  75                  80

Ala Gly Ala Gly Ser Gly Ala Gly Ala Gly Ser Gly Ala Gly Ala Gly
                85                  90                  95

Ser Gly Ala Gly Ala Gly Ser Gly Ala Gly Ala Gly Ser Gly Val Gly
            100                 105                 110

Val Pro Gly Val Gly Val Pro Gly Val Gly Val Pro Gly Val Gly Val
        115                 120                 125

Pro Gly Lys Gly Val Pro Gly Val Gly Val Pro Gly Val Gly Val Pro
    130                 135                 140

Gly Val Gly Val Pro Gly Ala Gly Ala Gly Ser Gly Ala Gly Ala Gly
145                 150                 155                 160

Ser Gly Ala Gly Ala Gly Ser Gly Ala Gly Ala Gly Ser Gly Ala Gly
                165                 170                 175

Ala Gly Ser Gly Ala Gly Ala Gly Ser Gly Val Gly Val Pro Gly Val
            180                 185                 190

Gly Val Pro Gly Val Gly Val Pro Gly Val Gly Val Pro Gly Lys Gly
        195                 200                 205

Val Pro Gly Val Gly Val Pro Gly Val Gly Val Pro Gly Val Gly Val
```

```
                210                 215                 220
Pro Gly Ala Gly Ala Gly Ser Gly Ala Gly Ala Gly Ser Gly Ala Gly
225                 230                 235                 240
Ala Gly Ser Gly Ala Gly Ala Gly Ser Gly Ala Gly Ala Gly Ser Gly
                245                 250                 255
Ala Gly Ala Gly Ser Gly Val Gly Val Pro Gly Val Gly Val Pro Gly
                260                 265                 270
Val Gly Val Pro Gly Val Gly Val Pro Gly Lys Gly Val Pro Gly Val
            275                 280                 285
Gly Val Pro Gly Val Gly Val Pro Gly Val Gly Val Pro Gly Ala Gly
            290                 295                 300
Ala Gly Ser Gly Ala Gly Ala Gly Ser Gly Ala Gly Ala Gly Ser Gly
305                 310                 315                 320
Ala Gly Ala Gly Ser Gly Ala Gly Ala Gly Ser Gly Ala Gly Ala Gly
                325                 330                 335
Ser Gly Val Gly Val Pro Gly Val Gly Val Pro Gly Val Gly Val Pro
                340                 345                 350
Gly Val Gly Val Pro Gly Lys Gly Val Pro Gly Val Gly Val Pro Gly
            355                 360                 365
Val Gly Val Pro Gly Val Gly Val Pro Gly Ala Gly Ala Gly Ser Gly
            370                 375                 380
Ala Gly Ala Gly Ser Gly Ala Gly Ala Gly Ser Gly Ala Gly Ala Gly
385                 390                 395                 400
Ser Gly Ala Gly Ala Gly Ser Gly Ala Gly Ala Gly Ser Gly Val Gly
                405                 410                 415
Val Pro Gly Val Gly Val Pro Gly Val Gly Val Pro Gly Val Gly Val
                420                 425                 430
Pro Gly Lys Gly Val Pro Gly Val Gly Val Pro Gly Val Gly Val Pro
            435                 440                 445
Gly Val Gly Val Pro Gly Ala Gly Ala Gly Ser Gly Ala Gly Ala Gly
            450                 455                 460
Ser Gly Ala Gly Ala Gly Ser Gly Ala Gly Ala Gly Ser Gly Ala Gly
465                 470                 475                 480
Ala Gly Ser Gly Ala Gly Ala Gly Ser Gly Val Gly Val Pro Gly Val
                485                 490                 495
Gly Val Pro Gly Val Gly Val Pro Gly Val Gly Val Pro Gly Lys Gly
                500                 505                 510
Val Pro Gly Val Gly Val Pro Gly Val Gly Val Pro Gly Val Gly Val
            515                 520                 525
Pro Gly Ala Gly Ala Gly Ser Gly Ala Gly Ala Gly Ser Gly Ala Gly
            530                 535                 540
Ala Gly Ser Gly Ala Gly Ala Gly Ser Gly Ala Gly Ala Gly Ser Gly
545                 550                 555                 560
Ala Gly Ala Gly Ser Gly Val Gly Val Pro Gly Val Gly Val Pro Gly
                565                 570                 575
Val Gly Val Pro Gly Val Gly Val Pro Gly Lys Gly Val Pro Gly Val
            580                 585                 590
Gly Val Pro Gly Val Gly Val Pro Gly Val Gly Val Pro Gly Ala Gly
            595                 600                 605
Ala Gly Ser Gly Ala Gly Ala Gly Ser Gly Ala Gly Ala Gly Ser Gly
            610                 615                 620
Ala Gly Ala Gly Ser Gly Ala Gly Ala Gly Ser Gly Ala Gly Ala Gly
625                 630                 635                 640
```

-continued

Ser Gly Val Gly Val Pro Gly Val Gly Val Pro Gly Val Gly Val Pro
        645                 650                 655

Gly Val Gly Val Pro Gly Lys Gly Val Pro Gly Val Gly Val Pro Gly
        660                 665                 670

Val Gly Val Pro Gly Val Gly Val Pro Gly Ala Gly Ala Gly Ser Gly
        675                 680                 685

Ala Gly Ala Gly Ser Gly Ala Gly Ala Gly Ser Gly Ala Gly Ala Gly
        690                 695                 700

Ser Gly Ala Gly Ala Gly Ser Gly Ala Gly Ala Gly Ser Gly Val Gly
705                 710                 715                 720

Val Pro Gly Val Gly Val Pro Gly Val Gly Val Pro Gly Val Gly Val
                725                 730                 735

Pro Gly Lys Gly Val Pro Gly Val Gly Val Pro Gly Val Gly Val Pro
        740                 745                 750

Gly Val Gly Val Pro Gly Ala Gly Ala Gly Ser Gly Ala Gly Ala Gly
        755                 760                 765

Ser Gly Ala Gly Ala Gly Ser Gly Ala Gly Ala Gly Ser Gly Ala Gly
        770                 775                 780

Ala Gly Ser Gly Ala Gly Ala Gly Ser Gly Val Gly Val Pro Gly Val
785                 790                 795                 800

Gly Val Pro Gly Val Gly Val Pro Gly Val Gly Val Pro Gly Lys Gly
                805                 810                 815

Val Pro Gly Val Gly Val Pro Gly Val Gly Val Pro Gly Val Gly Val
                820                 825                 830

Pro Gly Ala Gly Ala Gly Ser Gly Ala Gly Ala Gly Ser Gly Ala Gly
        835                 840                 845

Ala Gly Ser Gly Ala Gly Ala Gly Ser Gly Ala Gly Ala Gly Ser Gly
        850                 855                 860

Ala Gly Ala Gly Ser Gly Val Gly Val Pro Gly Val Gly Val Pro Gly
865                 870                 875                 880

Val Gly Val Pro Gly Val Gly Val Pro Gly Lys Gly Val Pro Gly Val
                885                 890                 895

Gly Val Pro Gly Val Gly Val Pro Gly Val Gly Val Pro Gly Ala Gly
        900                 905                 910

Ala Gly Ser Gly Ala Gly Ala Gly Ser Gly Ala Gly Ala Gly Ser Gly
        915                 920                 925

Ala Gly Ala Gly Ser Gly Ala Gly Ala Gly Ser Gly Ala Gly Ala Gly
        930                 935                 940

Ser Gly Val Gly Val Pro Gly Val Gly Val Pro Gly Val Gly Val Pro
945                 950                 955                 960

Gly Val Gly Val Pro Gly Lys Gly Val Pro Gly Val Gly Val Pro Gly
                965                 970                 975

Val Gly Val Pro Gly Val Gly Val Pro Gly Ala Gly Ala Gly Ser Gly
        980                 985                 990

Ala Gly Ala Gly Ser Gly Ala Gly Ala Gly Ser Gly Ala Gly Ala Gly
        995                 1000                1005

Ser Gly Ala Gly Ala Gly Ser Gly Ala Gly Ala Gly Ser Met Asp Pro
        1010                1015                1020

Gly Arg Tyr Gln Asp Leu Arg Ser His His His His His
1025                1030                1035

NANOCOMPOSITES OF REPEAT SEQUENCE PROTEINS AND PHYLLOSILICATE CLAYS AND THEIR PREPARATION

CROSS REFERENCES TO RELATED APPLICATIONS

The present application claims priority to U.S. Provisional Patent Application No. 60/710,308, filed Aug. 22, 2005.

This invention was made in the performance of a Cooperative Research and Development Agreement with the Department of the Air Force. The Government of the United States has certain rights to use the invention.

FIELD OF THE INVENTION

The present invention relates to nanocomposites formed from the combination of repeat sequence protein polymers and layered silicates. The invention also provides for methods for the synthesis of such nanocomposite materials.

BACKGROUND OF THE INVENTION

The combination of polymers and inorganic filler materials is known for the production of nanocomposite materials with improved mechanical, thermal and barrier properties as compared to the unmodified polymer. A detailed discussion of nanocomposites can be found in Ajayan, P. M., *Nanocomposite Science and Technology* (Wiley, 2003).

The combination of polymers with layered silicates, also known as smectite clays or phyllosilicates, has been exploited as a means for the synthesis of nanocomposites. Comprehensive reviews on the subject are Alexandre and Dubois (2001) and Pinnavaia, T. J.; Beall, G. W. *Polymer Clay Nanocomposites* Wiley New York, 2000. Smectite clays are described in Grim, R. E. *Clay Mineralology* $2^{nd}$ edition; McGraw-Hill: New York 1968.

Several methods for the synthesis of polymer clay nanocomposites have been described in the art, for example Nylon/clay composites first described by Usuki et al. (1993). A. Usuki, et al., "Synthesis of nylon 6-clay hybrid", J. Mater. Res., vol. 8, No. 5, May 1993, pp. 1179-1184. In this process nylon and montmorillonite are combined at high temperature to give an exfoliated nanocomposite with improved material properties relative to the polymer alone.

A biodegradable thermoplastic material comprising a natural polymer, a plasticizer and an exfoliated clay having a layered structure and a cation exchange capacity of from 30-350 milliequivalents per 100 grams is described in U.S. Pat. No. 6,811,599 B2. The natural polymer is a polysaccharide.

A smectite clay modified with an organic chemical composition and a polymer is described in U.S. Pat. No. 6,521,690.

Nanocomposites formed from phyllosilicates and the synthetic homopolymer poly-L-lysine have been described. (Krikorian, V. et al. *J. Polym. Sci. B: Polym. Phys.* 2002, 40, 2579). Soy protein isolate has also been incorporated into nanocomposites containing sodium montmorillonite clay (Chen, P. and Zhang, L. *Biomacromolecules*, 2006, 7, 1700).

Proteins make up the main structural elements of most organisms, using complex sequences of amino acids that lead to wide arrays of functionalities. One of the most intensely studied structural proteins, *Bombyx mori* silkworm silk, has generated significant interest because of its remarkable mechanical properties, which rival even spider silk. Elastin, another well-known structural protein, is found predominantly in the body's arterial walls, the lungs, intestines, and skin. Silk elastin like protein (SELP) is a recombinant protein consisting of alternating blocks of silk-like and elastin-like amino acids. The mechanical properties of recombinant proteins like SELP are often inferior to structural proteins found in nature.

The use of recombinant proteins in in-vivo applications and in applications outside of the body may demand improvements and alterations in a wide variety of properties, including high temperature mechanical behavior.

SUMMARY OF THE INVENTION

The invention is directed to compositions comprising nanocomposites of a phyllosilicate and one or more repeat sequence protein polymers. In one embodiment of the invention, the phyllosilicate is $Na^+$ Montmorillonite (MMT), a smectite clay and the repeat sequence protein polymer is a co-polymer comprising sequences derived from silk and elastin termed SELP. In yet another embodiment of the invention the repeat sequence protein polymer is a chemically modified SELP analogue whereby the protein is reacted with succinic anhydride. In another embodiment of the invention the phyllosilicate is attapulgite. In yet another embodiment of the invention, an additive, for example, a plasticizer, or a protein cross linking agent, or a plasticizer and a cross linking agent is added to the phyllosilicate and the repeat sequence protein polymer.

The compositions of the present invention are nanocomposites that demonstrate material property alterations and/or enhancements relative to the RSPP alone.

The nanocomposites are dispersions of phyllosilicate sheets within a protein matrix. The dispersion, or exfoliation, is achieved by interactions between the positively charged lysine residues of the protein and the negatively charged phyllosilicate sheets, in addition to other polar functionalities within the protein structure.

Without wishing to be bound by any particular theory, it is believed that the electrostatic character of the protein dominates long-range particle-particle interactions, and that the hydrogen bonding character of the protein dominates local interactions between the protein and the phyllosilicate material. Specifically, cationic charged proteins result in an exfoliated morphology, while the presence of anionic protein residues affects the morphology of the nanocomposite by generating repulsive interactions with MMT sheets that may result in a weak clustering or agglomeration of MMT in solution that manifests as at least some non-uniformity in the solid state.

The nanocomposites of the present invention may be tailored to have altered and/or improved elasticity as shown by elastic modulus values that are at least 10%, at least 20%, at least 30%, at least 40%, at least 50%, at least 60%, at least 70%, at least 80%, and at least 90% greater than the elastic modulus values of the RSPP alone. The nanocomposites also may be designed to have altered tensile properties, altered morphology, altered zeta potential, and or altered coefficient of thermal expansion.

The protein-based nanocomposite of repeat sequence protein polymer and phyllosilicate produces a repeat sequence protein polymer with mechanical properties suitable for use of the composite as suture material, as a tissue scaffold, artificial tissue, or biodegradable structural material, including industrial materials.

The nanocomposites of the present invention may also retain variable percentages of the water, or other solvents used to make the nanocomposites as well as other additives selected to tailor properties of the nanocomposites.

This invention also describes methods for the formation of nanocomposites consisting of a phyllosilicate and a repeat sequence protein polymers. The method comprises suspending a phyllosilicate in deionized water or buffered water, with or without an additional solvent; and adding a repeat sequence protein polymer to the phyllosilicate suspension with mixing and/or sonication. The resulting mixture may be cast into a vessel and allowed to dry.

The amount of SELP material added to the phyllosilicate suspension may be selected to provide a nanocomposite with desired material properties. For example, a nanocomposite with desired elastic modulus values, or tensile strength values, may be made by varying the amount of SELP in the composite.

BRIEF DESCRIPTION OF THE DRAWINGS

FIGS. 3A and 3B are, respectively, graphs showing the elastic modulus and the coefficient of thermal expansion (CTE) of nanocomposites of the present invention.

FIG. 4 is a graph showing the zeta potential for aqueous suspensions of a phyllosilicate having increasing concentrations of repeat sequence protein polymer.

FIG. 5 is low and high magnification TEM images of nanocomposites of the present invention.

FIG. 6 is a graph showing stress-strain curves for nanocomposites of the present invention, with a table listing the elastic modulus (GPa) and percent elongation to break (%) calculated from the curves.

DETAILED DESCRIPTION OF THE INVENTION

Figure 1:
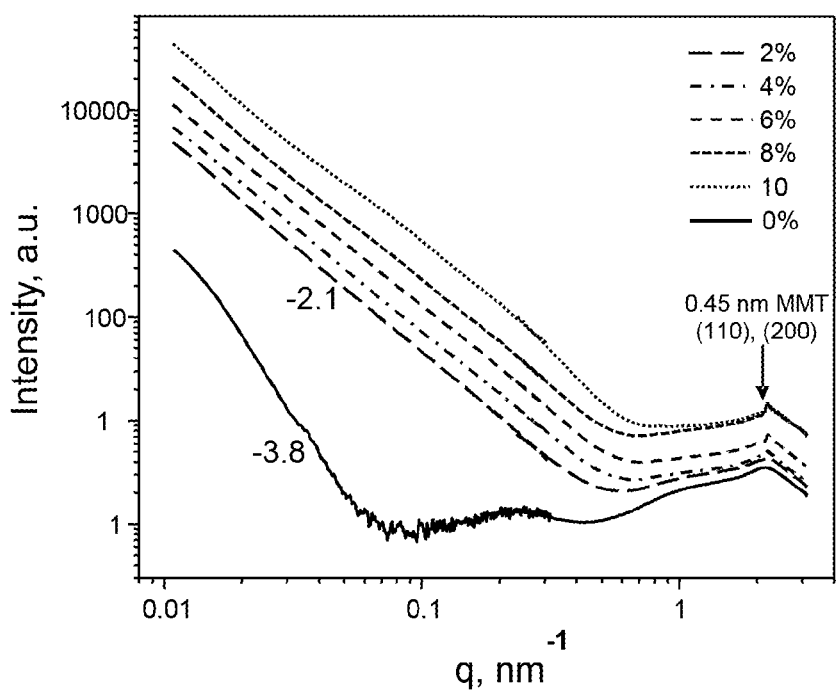
FIG. 1 is a graph showing X-ray scattering curves for nanocomposites of the present invention.

The present invention is directed to compositions that are nanocomposites of a phyllosilicate material and one or more repeat sequence protein polymers. In one embodiment of the invention, the phyllosilicate material is a smectite clay, for example, montmorillonite (MMT) clay, and the repeat sequence protein polymer is a co-polymer having sequences derived from silk and elastin, termed SELP. In yet another embodiment of the invention the repeat sequence protein polymer is a chemically modified SELP analogue whereby the protein is reacted with succinic anhydride.

The nanocomposites of the present invention are highly exfoliated materials produced under controlled conditions. The invention further includes methods for the formation of nanocomposites of a phyllosilicate and a repeat sequence protein polymer. The method suspends a phyllosilicate clay in water with or without a solvent; adds a repeat sequence protein polymer to the phyllosilicate suspension with mixing and/or sonication. The resulting mixture may be cast into a vessel and dried, retaining varying amounts of water or other solvent. Additives may be used and added to select properties of the nanocomposites.

DEFINITIONS

For purposes of this invention, the following definitions shall apply:

"Elastic modulus", or modulus of elasticity means a measurement that expresses the ability of a material to return to its original dimension after the removal of stresses, calculated by the formula $E=S/\delta$, where S is the unit stress and $\delta$ is the unit strain. The nanocomposites of the present invention have an elastic modulus that is at least 10%, at least 20%, at least 30%, at least 40%, at least 50%, at least 60%, at least 70%, at least 80%, and at least 90% greater than the elastic modulus of the RSPP without the addition of the phyllosilicate material.

An "Exfoliated nanocomposite" means a composite morphology where the layers of the phyllosilicate component are dispersed or displaced from the generally intercalated layered structure found in the starting phyllosilicate material. A "highly exfoliated nanocomposite" exhibits a morphology that is generally homogeneous because substantial layer dispersion has occurred so that the composite cannot be shown to have distinct phyllosilicate and RSPP phases.

Without wishing to be bound by any particular theory, it is believed that the electrostatic character of the protein dominates long-range particle-particle interactions, and that the hydrogen bonding character of the protein dominates local interactions between the protein and the phyllosilicate material. Specifically, cationic charged proteins result in an exfoliated morphology, while the presence of anionic protein residues affects the morphology of the nanocomposite by generating repulsive interactions with MMT sheets that may result in a weak clustering or agglomeration of MMT in solution that manifests as at least some non-uniformity in the solid state.

"Material properties" means tensile strength, elastic modulus, morphology, and altered and/or improved thermal properties.

The nanocomposites of the present invention demonstrate an alteration and/or improvement, when compared to repeat sequence protein polymers alone, of one or more material properties.

A "nanocomposite" means a composite composed of two or more physically distinct materials in close contact, where at least one of the two or more phases exhibits at least one dimension that is in the nanometer size range (i.e. smaller than 100 nanometers). The close contact between phases in a nanocomposite underlies the unique properties of this class of materials relative to conventional composite materials. Ajayan, P. M., *Nanocomposite Science and Technology* (Wiley, 2003).

"Tensile Strength" as applied to a composite film means the maximum stress which can be applied in a tension test prior to breakage (failure) of the film. Tensile strength is expressed in Pascals (MPa) or pounds per square inch (psi).

"Percent elongation-to-break", sometimes referred to as strain to break, is the strain on a material when it breaks and is expressed as a percent. Tensile properties includes tensile strength and percent elongation-to-break.

"Zeta potential" means the electrical potential that is generated by the accumulation of ions at the surface of a colloidal particle.

Repeat Sequence Protein Polymers

The repeat sequence protein polymer (RSPP) can be any modified polypeptide with at least one distinct domain repeated throughout the entire sequence two or more times.

The at least two distinct repeating domains of the RSPPs suitable for the present invention may be derived from a natural, chemically synthesized and/or modified, recombinant protein, or mixtures thereof. For example, the repeating sequence units may be derived from modifying a natural structure supporting materials such as silk, elastin, and collagen. Alternatively, the repeating sequence units may be derived from synthetic structures.

One skilled in the art will appreciate the various naturally occurring proteins containing repeating sequence units, which can be modified and used for designing and producing the repeat sequence protein polymers of the present invention, any of which may be employed herein. Specifically, there are more than six hundred repeating amino acid sequence units known to exist in biological systems. The natural OR synthetic protein repeating amino acid sequence units are derived by making modifications to elastin, collagen, abductin, byssus, extensin, flagelliform silk, dragline silk, gluten high molecular weight subunit, titin, fibronectin, leminin, gliadin, glue polypolypeptide, ice nucleating protein, keratin mucin, RNA polymerase II, resilin or a mixture thereof.

RSPP repeating sequence units for the natural or synthetic materials listed above are described and the amino acid sequences are shown in WO 04080426A1, which is incorporated herein in its entirety.

The repeat sequence protein polymer (RSPP) formula comprises:

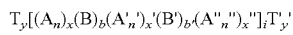

$$T_y[(A_n)_x(B)_b(A'_{n'})_{x'}(B')_{b'}(A''_{n''})_{x''}]_i T'_{y'}$$

wherein: T and T' each comprise an amino acid sequence of from about 1 to about 100 amino acids, wherein the amino acid sequence of T' is the same as or different from the amino acid sequence of T; y and y' are each an integer from 0 to 1, wherein the integer of y' is the same as or different from the integer of y; A, A' and A" are each individual repeating amino acid sequence units comprising from about 3 to about 30 amino acids, wherein the amino acid sequence of A' and the amino acid sequence of A" are the same as or different from the amino acid sequence of A; n, n', and n" are each integers of at least 2 and not more than 250; x, x' and x" are each 0 or an integer of at least 1, wherein each integer varies to provide for at least 30 amino acids in the A', A' and A" individual amino acid sequence repeating units, and wherein the integer of x' and the integer of x" are the same as or different from the integer of x and x, x', and x" cannot all be zero; B and B' each comprise an amino acid sequence of from about 4 to about 50 amino acids, wherein the amino sequence of B' is the same as or different from the amino acid sequence of B; b and b' are each an integer from 0 to 3, wherein the integer of b' is the same as or different from the integer of b; and i is an integer from 1 to 500.

The repeating amino acid sequence units may comprise identical repeating sequence units or may comprise different repeating sequence unit combinations, which join together to form a block copolymer or an alternating block copolymer. Additionally, the individual repeating amino acid sequence units of the repeat sequence protein polymer comprise from about 3 to about 30 amino acids or from about 3 to about 8 amino acids. Moreover, the same amino acid may appear at least twice in the same repeating sequence unit.

It will be further understood by those having skill in the art that the repeat sequence protein polymers of the present invention may be monodispersed or polydispersed. For purposes of defining and describing the present invention, "monodispersed" polymers are polymers having a single defined molecular weight. For purposes of defining and describing the present invention, "polydispersed" polymers are polymers that have been subjected to proteolysis or other means of subdivision, or were produced or modified in such a manner as to give rise to a distribution of molecular weights.

In one embodiment, the copolymers are combinations of silk units and elastin units to provide silk-elastin copolymers having properties distinctive from polymers having only the same monomeric unit.

A silk-elastin polymer, SELP47K, may be used as the repeat sequence protein polymer of the present invention. The SELP47K is a homoblock protein polymer that consists exclusively of silk-like crystalline blocks and elastin-like flexible blocks. SELP47K is a modified material of 70% proline, valine, and alanine, and has hydrophobic characteristics. The repeat sequence protein polymer may also comprise SELP 47-E13, SELP 47R-3, SELP 47K-3, SELP 47 E-3, SELP 67K, and SELP 58.

In one embodiment of the invention, the structure of the silk elastin-like protein is Head-$(S_2E_3E_KE_4S_2)_{13}$-Tail (SEQ ID NO:6), where S is the silk-like sequence of amino acids GAGAGS (SEQ ID NO:1), E is the elastin-like sequence GVGVP (SEQ ID NO:2), and $E_K$ is the elastin like sequence modified with a lysine residue GKGVP (SEQ ID NO:3). The head sequence of amino acids is MDPVVLQRRD WENPGVTQLN RLAAHPPFAS DPM (SEQ ID NO:4) and the tail sequence is GAGAM DPGRYQDLRS HHHHHH (SEQ ID NO:5). The copolymer contains 886 amino acids, with 832 amino acids in the repeating sequence unit. The SELP47K has a molecular weight of about 70,000 Daltons, and a pI of 10.5. The properties of other SELP variants are shown below in Table 1.

TABLE 1

SELP variants, properties.

| Variant Name | Number of Subunits | Lysine Substitution | Molecular Weight (Da) | Isoelectric Point | SEQ ID NO |
|---|---|---|---|---|---|
| SELP47E | 13 | Glutamic Acid | 70,212 | 4.16 | 7 |
| SELP47K-3 | 3 | none | 20,748 | 9.52 | 8 |
| SELP47R-3 | 3 | Arginine | 20,960 | 10.5 | 9 |
| SELP47E-3 | 3 | Glutamic Acid | 20,879 | 5.9 | 10 |
| SELP27K | 13 | none | 59,401 | 10.53 | |
| SELP37K | 13 | none | 64,605 | 10.53 | |
| SELP58 | 13 | none | 74,765 | 6.7 | 11 |
| SELP67K | 13 | none | 80,347 | 10.53 | 12 |

One skilled in the art will appreciate the various methods for producing the repeat sequence protein polymers of the present invention, any of which may be employed herein. For example, the repeat sequence protein polymer may be produced by generally recognized methods of chemical synthesis, for example, L Andersson et. al., *Large-scale synthesis of peptides*, Biopolymers 55(3), 227-50 (2000)); genetic manipulation (for example, J. Cappello, Genetically Engineered Protein Polymers, Handbook of Biodegradable Polymers, Domb, A. J.; Kost, J.; Wiseman, D. (Eds.), Harvard Academic Publishers, Amsterdam; pages 387-414); and enzymatic synthesis (for example, C. H. Wong & K. T. Wang, *New Developments in Enzymatic Peptide Synthesis*, Experientia 47 (11-12), 1123-9 (1991)). For example, the repeat sequence protein polymers of the present invention may be produced using the methods described in U.S. Pat. Nos. 5,243,038; 6,355,776; and WO 07080426A1 the disclosures of which are incorporated by reference herein. In another example, the repeat sequence protein polymers may be produced utilizing non-ribosomal peptide synthase (for example, H. V. Dohren, et al., Multifunctional Peptide Synthase, Chem. Rev. 97, 2675-2705 (1997).

The *E. coli* strains containing a specific silk-elastin repeat sequence protein copolymer SELP47K, SELP37K and SELP27K recombinant DNA were also obtained from Protein Polymer Technologies, Inc. of San Diego, Calif. SELP67K, SELP58, SELP37K and SELP27K variant proteins were produced in 14 L fed batch culture using standard SELP47K production protocols, as described above. Proteins were purified and characterized as follows: 40 grams of cell pastes collected from 14 L cultures were lysed via French-press followed by the addition of polyethyleneimine (0.8 w/v %). Centrifugation was used to separate the cellular debris from the cell extract. SELP polymers were precipitated from the cell extract using ammonium sulfate (30% saturation), collected by centrifugation and reconstituted in water.

The protocol used for the genetic engineering of variants SELP47E, SELP47K-3, SELP47R-3, and SELP47E-3 is a modification of a commercially available kit designed to create single base pair changes in multiple sites along a particular DNA sequence (QUIKCHANGE® Multi (Site-Directed Mutagenesis Kit), Stratagene cat #200513). The standard protocol involves the construction of single direction 5' phosphorylated primers that will hybridize to plasmid template regions of interest and incorporate point mutations. Thermocycling is employed that includes a ligation reaction designed to link the multiple primers during each round of synthesis.

Phyllosilicates

The layered silicate materials suitable for the present invention are phyllosilicates, frequently referred to as smectite clays. Phyllosilicates have a multiple layer structure with the layers having a thickness of between about 3 Angstroms to about 10 Angstroms. Each two-dimensional layer is made up of two silica tetrahedra sheets arranged on either side of an octahedral alumina sheet. The multiple layers are separated by cations. A number of phyllosilicates have a cation exchange capacity of between 20 and 250 mEq per 100 g.

The layered phyllosilicates are swellable clays in that they expand when exposed to liquids such as water, or other solvents with the ability to act as hydrogen bond acceptors and/or donors, thereby increasing the space between the layers. Examples include, but are not limited to montmorillonite, bentonite, hectorite, saponite, beidellite, attapulgite, and stevensite.

In one embodiment, the phyllosilicate is sodium montmorillonite, or its ion exchanged form, which may be obtained in the sodium form by utilizing naturally occurring clay. Sodium montmorillonite consists of negatively charged, 1 nm thick aluminosilicate layers with exchangeable sodium cations on the surface. The sheets are approximately 100 nm in diameter. In another embodiment of the present invention, the phyllosilicate is attapulgite.

Those skilled in the art will recognize that phyllosilicate clays that have been processed to remove non-clay materials can be converted to the sodium form if desired by either running a clay slurry through a cation exchange resin; or, by forming a mixture of clay, water and a water-soluble sodium compound and subjecting the mixture to shear.

The concentration by weight of phyllosilicate used in the present nanocomposite invention is about 0.1 to about 9-9%, about 0.1 to about 50%, about 1% to about 20%, about 1% to about 10%, and about 4% to about 6%.

The nanocomposites may retain variable amounts of the water or other solvents used to make the composites. For instance, the nanocomposites may retain from about 0.1% to about 90%, about 1% to about 50%, about 1% to about 25%, about 1% to about 15%, about 1% to about 10%, about 5% to about 20%, and about 5% to about 10% of water or other solvents.

The nanocomposites may include additives to tailor and vary properties. For instance, additives may be salts, onium ions, plasticizers, anti-microbials, reinforcing agents, protein cross linking agents, growth factors, preservatives, nanoparticles, nanofibres, chaotropic agents and electrolytes.

Plasticizers decrease the glass transition temperature of nanocomposite films and improve film flexibility, particularly at room temperature. The concentration of such plasticizers is from about 2 wt % to about 10 wt % of the total solids in suspension. Suitable plasticizers include polyethylene glycol (PEG) and a mono-, poly-, or di-saccharide, for example, trehalose. Common families of molecules that may also be used to plasticize nanocomposite films include adipic acid derivatives, azeic acid derivatives, benzoic acid derivatives, diphenyl derivatives, citric acid derivatives, epoxides, glycolates, isophthalic acid derivatives, maleic acid derivatives, phosphoric acid derivatives, phthalic acid derivatives, polyesters, trimelitates, etc. Specifically, water soluble plasticizers can be used such as citrate esters, triethyl citrate, triacetin, diethyl phthalate, glycerol, polyalkylene glycols such as polyethylene glycol, trehalose, polysaccharaides, polysuccinimide and poly aspartate.

Protein crosslinkers such as glutaraldehyde can be used to stabilize the films from solvent attack, as well as increase the effective molecular weight. Concentrations of approximately 0.6% to approximately 4% are typically used for glutaraldehyde crosslinking. Other homofunctional and heterobifunctional protein crosslinkers that react primarily with protein amines, sulfhydryls and carboxyl groups may be used. Homobifunctional protein crosslinkers that react with sulfhyhryl groups include 1,4-bis[3-(2-pyridyldithio)propionamido]butane (DPDPB), bis[2-(N-succinimidyl-oxycarbonyloxy)ethyl]sulfone(BSOCOES), ethylene glycol disuccinate di(N-succinimidyl)ester (EGS). Dimethyl 3,3'-dithiopropionimidate dihydrochloride is a homobifunctional reagent which typically reacts with primary amines to form amidine bonds. Bis[2-(4-azidosalicylamido)ethyl]disulfide (BASED) is a photoactive crosslinker with amine reactivity. Sebacic acid bis(N-succinimidyl)ester (DSS) is a homobifunctional crosslinker with amine reactivity. Sulfosuccinimidyl 4-(N-maleimidomethyl)cyclohexane-1-carboxylate) (SulfoS-MCC) is a heterobifunctional crosslinker that interacts with amine and sulfhydryl groups. Dithiobis(succinimidylpropionate) (DSP) is homobifunctional and reactive towards amino groups. Spacer arms can be used in these molecules if the distance between reactive groups in the protein is unknown. Intermediate crosslinkers such as ethyl-3-(dimethylaminopropyl)carbodiimide (EDC) can also be used to modify reactive groups for later crosslinking or functionalization.

The following examples are included to illustrate embodiments of the invention and are not intended to be limiting thereof.

EXAMPLES

Example 1

Production of Silk-Elastin Like Protein (SELP)

Monodispersed silk-elastin protein polymer SELP47K was produced by fermenting a recombinant *E. coli* strain to produce a cell-paste containing monodispersed SELP47K as described in US2004/0180027A1. The cell-paste is placed in ice cold water and homogenized to make the cell extract. The cell-extract is mixed with polyethyleneimine and a filter-aid and allowed to sit at 7° C. for one hour. The polyethyeleneimine causes precipitation of cell debris and a significant amount of E. coli proteins. The SELP47K containing reaction mixture is then filtered using a Rotary Drum Vacuum Filter (RVDF). The filtered SELP47K solution is then mixed with ammonium sulfate to 25% saturation, which leads to precipitation of SELP47K. Precipitated SELP47K and mother liquor is mixed with a filter-aid and again filtered using RVDF. The RVDF cake containing SELP47K and filter-aid is mixed with cold water to dissolve the SELP47K. This precipitation and solubilization step is repeated to improve the purity profile of the SELP47K. Purified monodispersed SELP47K is then water-exchanged until the conductivity of SELP solution reached 50 µS/cm$^2$. The monodispersed SELP solution was then concentrated to 10% wt/vol and then lyophilized to make powdered monodispersed SELP47K protein polymer. The material was stored at −70° C. until needed for application testing.

Example 2

Preparation of Succinylated SELP

Succinylated SELP was prepared from a solution of SELP (0.7 g) in 25% aqueous acetonitrile (10 mL) that was treated with succinic anhydride (152 mg) at room temperature. Sodium hydroxide solution (3M) was added dropwise in order to maintain the pH between 7 and 8 during the course of the reaction. After 3 hours an aliquot was found to be unreactive towards ninhydrin indicating the derivatization of the available amino functionalites. The sample was dialyzed against water (3×2 L) overnight and then freeze dried to give a spongy white solid (0.62 g).

Example 3

Preparation of the RSPP/Phyllosilicate Solutions and Films

Cloisite® Na+ Montmorillonite (MMT) phyllosilicate in powder form (Southern Clay, cation exchange capacity [CEC] 92 meq/100 g) was added to deionized water to form 0.1-1.0 wt % suspensions. The water/MMT suspensions were then sonicated using a probe sonicator for approximately 10 minutes. For zeta potential measurements, SELP in powder form was slowly added to the MMT suspensions. For preparation of thin films, SELP was dissolved in deionized water to form a 5 wt % solution, and was added to the MMT suspension. The mixtures were then cast into polystyrene weighing dishes and dried for several days. The resulting films were freestanding, optically clear, approximately 5 cm in diameter, and the total amount of solid in each film was approximately 100 mg. The final amounts of MMT in the nanocomposite material were 0%, 2%, 4%, 6%, 8% and 10% on a dry weight basis.

Nanocomposites using the phyllosilicate attapulgite in powder form were also prepared by adding the attapulgite to deionized water and then mixing the suspension with SELP. Films were prepared as described above.

Example 4

Methods for Characterizing Material Properties of the Nanocomposite

Zeta Potential

Zeta potential measurements of the nanocomposite liquid solvent mixtures were performed on a ZetaPALS instrument (Brookhaven Instruments Corp., NY) at room temperature. At each MMT concentration, the average value was taken from 10 measurements. 0.01 wt % and 0.1 wt % MMT in water suspensions were stirred overnight, and then allowed to settle for several days. Samples for zeta potential measurements were then taken from the supernatant of the settled suspensions. SELP or succinylated SELP powder was added to the suspensions in various amounts. The zeta potential results were generally similar for both the 0.01 and 0.1 wt % suspensions at the same relative concentrations.

X-Ray Diffraction Profiles

Small angle x-ray scattering profiles were collected at beamline X27C of a National Synchrotron Light Source instrument with an evacuated beam path, a camera length of 1870 mm, an x-ray wavelength of 0.1366 nm, and a Mar-CCD (Charge coupled device) large area detector (Mar USA, Evanston, Ill.). Wide angle scattering was done using a Rigaku™ rotating anode operating at 50 kV with a Statton camera (camera length 73 mm), imaging plates held under vacuum, and an x-ray wavelength of 0.15418 nm. Two-dimensional patterns were analyzed using the Fit2D software (A. Hammersley, European Synchrotron Radiation Facility).

Transmission Electron Microscopy (TEM)

Transmission electron microscopy was performed on a Philips™ CM200-FEG instrument operating at 200 kV. Films were cut into ~25 mm$^2$ size sections, embedded in Spurr (Electron Microscopy Sciences, Hatfield, Pa.) epoxy and cured at room temperature overnight. Cross sectional microtomy was done in on a RMC PowerTome™ with a diamond knife at room temperature. Section thickness was 100-150 nm.

Tensile Tests

Films were cut into strips approximately 5×35 mm for tensile strength testing. Five tests were run on each sample concentration. The slope of the stress-strain curve at 0.25% strain was used to calculate the elastic modulus. The percentage elongation to break, or strain to break was also measured as a percentage value.

Thermal Mechanical Analysis

In thermal mechanical analysis, the coefficient of thermal expansion (CTE) was measured as the slope of the sample's length at constant stress vs. temperature curve, divided by the original length of the sample. This slope was measured over a 2° C. temperature span in the rubbery regime (>200° C.)

Example 5

Material Properties of the Nanocomposites

X-Ray Diffraction

FIG. 1b shows scattering curves in the small-angle and wide-angle regimes. There was no interlayer spacing near 1.2 nm, as is seen in the MMT powder control. Peaks arising from the interatomic (intra-sheet) MMT spacings as well as the broad peaks from the SELP can be seen at scattering vector (q) values greater than 1 nm$^{-1}$. In the small angle regime (q<1 nm$^{-1}$) there is a very uniform scattering profile with no evidence for peaks at these larger length scales.

The results indicate that there is no intermediate structure, where the protein chains are intercalated between the MMT sheets in an ordered fashion. The WAXS regime ($q>1$ nm$^{-1}$) shows that the SELP is not crystalline, as shown be the absence of the characteristic silk I peak at d=0.72 nm as well as the lack of any clear silk II β-sheet peaks.

TEM

Figure 2:
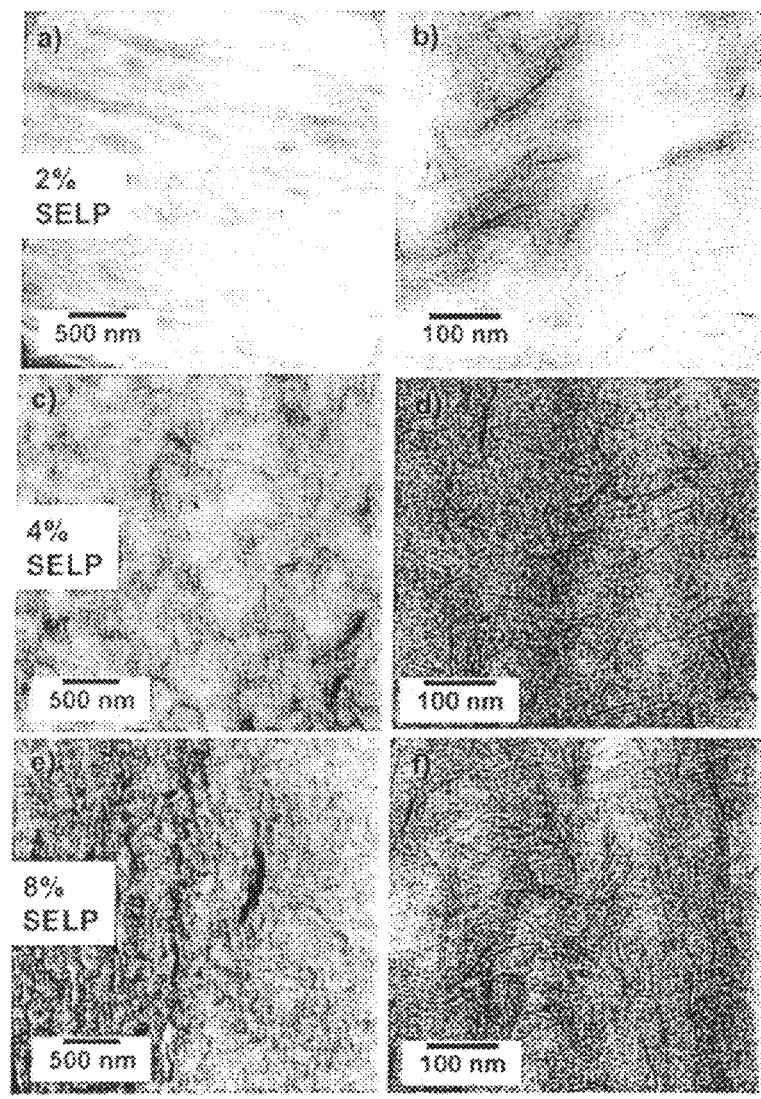
FIG. 2 is low and high magnification transmission electron microscopy (TEM) images of nanocomposites of the present invention.

FIG. 2 shows TEM micrographs from 150 nm thick cross-sections of 2%, 4% and 8% MMT in SELP nanocomposite samples. The high magnification micrographs (2b, d, f) show that the MMT is dispersed well in the SELP matrix, with the individual, 1 nm thick, MMT sheets visible. The density of MMT also appears to be quite uniform across the films from top to bottom, and along their length for several hundreds of microns (FIGS. 2a, c, e).

The TEM and X-ray diffraction data both support the findings of a highly exfoliated structure.

Tensile Properties

Film tensile tests showed an elastic modulus for the SELP alone control films of 2 GPa (FIG. 3a) and tensile strengths greater than 50 Mpa (Data not shown). As MMT concentration increased, an increase in the elastic modulus to nearly 3 GPa was seen up to loadings of 4-6%. At MMT loadings above 4-6%, the modulus dropped. While the modulus of the films was increased at 4% MMT, the films were found to be more brittle, with the percent elongation to break, or strain to break, decreasing from 0.044 (4.4%) at 0% MMT to 0.012 (1.2%) at 4% MMT.

Differential Scanning Calorimetry

Differential Scanning Calorimetry (DSC) showed no significant shift in the SELP glass transition with the addition of MMT. The $T_g$ remained near 180° C. regardless of the amount of MMT present, and this value is similar to the $T_g$ measured from dry films and fibers of silk and elastin.

Thermal Properties

Thermal mechanical analysis (TMA) was used to determine the coefficient of thermal expansion (CTE) in the rubbery region (>200° C.). The CTE showed a decrease with increasing amounts of MMT from 94×10$^{-3}$° C.$^{-1}$ in the SELP only control to as low as 49×10$^{-3}$° C.$^{-1}$ at 8% MMT loading (FIG. 3b). While DSC showed no evidence for a $T_g$ shift, the temperature at which the samples transitioned from glassy to rubbery behavior, as measured from the intersection of the slopes of the sample length vs. temperature curves in the glassy and rubbery regions, was seen to increase significantly with increasing MMT concentration. This temperature increased from 193° C. in the SELP to 213° C. in the 10% MMT/SELP samples.

Zeta Potential

FIG. 4 shows a plot of zeta potential at various weight ratios of SELP/MMT. The zeta potential of the pure MMT suspension and the SELP solution are plotted on the log-linear plot at SELP/MMT relative concentrations of 0.0001 and 10000, respectively. The zeta potential of sodium MMT in water, at a concentration of 0.1 wt %, is −42 mV (Southern™ Clay Na$^+$, 92 meq/100 g). The size of the MMT sheets, as measured by the median in the log-normal distribution of sizes measured from light scattering, was 90 nm. As SELP is added into the suspension in higher concentrations, the effective size and surface charge of the MMT sheets remains relatively unaltered until the weight ratio of SELP/MMT reaches about 1. The surface charge decreases in magnitude as SELP is adsorbed onto the MMT, the zeta potential goes toward zero, and is then neutralized at a SELP/MMT weight ratio of 8:1. The zeta potential of the system does not go far into the positive regime with the continued addition of SELP, because of the low overall positive charge of the protein (only 13 positively charged lysines out of 886 total residues). The zeta potential of the SELP solution (0.5-1 wt %) was measured to be +3 mV. The exfoliated composites had SELP/MMT weight ratios varying from 10:1 to 50:1, and it can be seen in FIG. 4 that the MMT charge is neutralized by the adsorbed protein at these ratios.

In the SELPsucc nanocomposites we see good dispersion at the nanometer length scale, as we saw in the SELP nanocomposites. X-ray scattering shows no MMT interlayer spacing and no intercalation peak. On larger length scales, however, some macroscopic phase separation in the SELPsucc can be seen, especially in low magnification TEM images. FIG. 5 shows electron micrographs of the SELPsucc samples and clear regions of MMT-rich and protein rich regions can be seen.

In aqueous solution, absorption of SELP on MMT sheets seems to readily occur, irrespective of a small fraction of ionic residues. However, these residues play a dominate role in determining the morphology of the nanocomposite because the anionic residues generate repulsive interactions with MMT sheets resulting in a weak clustering or agglomeration of MMT in solution that manifests in non-uniformity in the solid state.

Example 6

Preparation of Plasticized RSPP Nanocomposite Films

Plasticizers, including polyethylene glycol (PEG) and trehalose were used to decrease the glass transition temperature of the films and to improve film flexibility at room temperature. SELP solutions with MMT in deionized water were prepared as in example 3, and PEG (molecular weight 200 g/mol) was added in concentrations ranging from 2-10 wt % of the total solids in suspension. Samples were made containing 3% w/w of MMT, 2% w/w of PEG, and 95% w/w SELP were made and the tensile strength of these samples were compared to the tensile strength of SELP alone, as shown in FIG. 6. Common families of molecules that may also be used to plasticize these nanocomposite films include adipic acid derivatives, azeic acid derivatives, benzoic acid derivatives, diphenyl derivatives, citric acid derivatives, epoxides, glycolates, isophthalic acid derivatives, maleic acid derivatives, phosphoric acid derivatives, phthalic acid derivatives, polyesters, trimelitates, etc. Specifically, water soluble plasticizers can be used such as citrate esters, triethyl citrate, triacetin, diethyl phthalate, glycerol, polyalkylene glycols such as polyethylene glycol, trehalose, polysaccharides, polysuccinimide and poly aspartate.

Example 7

Preparation of Cross-Linked RSPP Nanocomposite Films

Protein crosslinkers were used to stabilize the films from solvent attack, as well as increase the effective molecular weight. After SELP/MMT films made according to Example 3 were dried, they were submerged in a 2.5 vol. % glutaraldehyde solution to crosslink for 18 hours. Concentrations of approximately 0.6%-4% were typically used for glutaraldehyde crosslinking. The films were then submerged in DI water for 2 hours for rinsing and subsequently dried. Concentrations of approximately 0.6% to approximately 4% are typically used for glutaraldehyde crosslinking.

What is claimed is:

1. A nanocomposite comprising a repeat sequence protein polymer and a phyllosilicate, wherein the repeat sequence protein polymer is a silk elastin like protein (SELP).

2. The nanocomposite of claim 1, wherein the phyllosilicate is selected from montmorillonite, bentonite, hectorite, saponite, beidellite, attapulgite, and stevensite.

3. The nanocomposite of claim 1 further comprising a plasticizer, a protein cross linking agent, or a plasticizer and a protein cross linking agent.

4. The nanocomposite of claim 3, wherein the plasticizer is selected from adipic acid derivatives, azeic acid derivatives, benzoic acid derivatives, diphenyl derivatives, citric acid derivatives, epoxides, glycolates, isophthalic acid derivatives, maleic acid derivatives, phosphoric acid derivatives, phthalic acid derivatives, polyesters, trimelitates, polyalkylene glycols, polysaccharides, disaccharides, and monosaccharides.

5. The nanocomposite of claim 3, wherein the plasticizer is polyethylene glycol or trehalose and the protein cross linking agent is glutaraldehyde.

6. The nanocomposite of claim 1 having at least one altered material property as compared to a material property of the repeat sequence protein polymer without the addition of the phyllosilicate.

7. The nanocomposite of claim 6, wherein the at least one altered material property is selected from tensile strength, elastic modulus, morphology, and coefficient of thermal expansion.

8. The nanocomposite of claim 7, having an exfoliated morphology.

9. The nanocomposite of claim 7, having a generally homogeneous morphology.

10. The nanocomposite of claim 7, wherein the elastic modulus of the nanocomposite is at least 10% greater than the elastic modulus of the repeat sequence protein polymer without addition of the phyllosilicate.

11. The nanocomposite of claim 7, wherein the coefficient of thermal expansion of the nanocomposite is less than a coefficient of thermal expansion of the repeat sequence protein polymer without addition of a phyllosilicate.

12. The nanocomposite of claim 1, wherein the nanocomposite has an altered zeta potential compared to a zeta potential of the phyllosilicate without addition of the repeat sequence protein polymer.

13. The nanocomposite of claim 4 comprising a plasticizer, the nanocomposite having an increased percentage elongation-to-break as compared to a percentage elongation-to-break of a nanocomposite without plasticizer.

14. The nanocomposite of claim 1, wherein the nanocomposite is a suture material.

15. The nanocomposite of claim 1, wherein the nanocomposite is a tissue scaffold material.

16. The nanocomposite of claim 1, wherein the nanocomposite is a biodegradable structural material.

17. A method for making a nanocomposite, the method comprising:
    selecting a repeat sequence protein polymer;
    selecting a phyllosilicate;
    placing the phyllosilicate in an aqueous liquid to form a suspension;
    mixing the repeat sequence protein polymer and the suspension; and
    allowing the at least one repeat sequence protein polymer mixed with the suspension to dry, wherein the repeat sequence protein polymer is a silk elastin like protein (SELP).

18. The method of claim 17, wherein the repeat sequence protein polymer mixed with the suspension is cast onto a surface.

19. The method of claim 17 further comprising adding a plasticizer, a protein cross linking agent, or a plasticizer and a protein cross linking agent.

20. The nanocomposite of claim 1 wherein the repeat sequence protein polymer is selected from the group consisting of SEQ ID No:6 through SEQ ID No:12.

* * * * *